(12) United States Patent
Lim et al.

(10) Patent No.: US 8,501,436 B2
(45) Date of Patent: Aug. 6, 2013

(54) METHOD FOR PREPARATION OF CARBAMIC ACID (R)-1-ARYL-2-TETRAZOLYL-ETHYL ESTER

(75) Inventors: Sang Chul Lim, Daejeon (KR); Moo Yong Uhm, Daejeon (KR); Nahm Ryune Cho, Daejeon (KR); Dae Won Lee, Siheung-si (KR); Ju Young Lee, Daejeon (KR); Hui Ho Kim, Daejeon (KR); Dong Ho Lee, Daejeon (KR); Hyun Seok Lee, Daejeon (KR); Se Il Lee, Incheon (KR)

(73) Assignee: SK Biopharmaceuticals Co. Ltd., Seoul (KR)

( * ) Notice: Subject to any disclaimer, the term of this patent is extended or adjusted under 35 U.S.C. 154(b) by 506 days.

(21) Appl. No.: 12/578,709

(22) Filed: Oct. 14, 2009

(65) Prior Publication Data
US 2010/0323410 A1 Dec. 23, 2010

(30) Foreign Application Priority Data

Jun. 22, 2009 (KR) .................. 10-2009-0055576

(51) Int. Cl.
*C12P 17/10* (2006.01)
*C12P 1/00* (2006.01)

(52) U.S. Cl.
USPC .............. 435/41; 435/25; 435/121; 435/135; 435/155

(58) Field of Classification Search
USPC 435/121, 41, 25, 135, 155; 548/253; 514/359
See application file for complete search history.

(56) References Cited

U.S. PATENT DOCUMENTS

| | | | |
|---|---|---|---|
| 5,276,154 A | 1/1994 | Hiyama et al. | |
| 5,391,495 A | 2/1995 | Patel et al. | |
| 5,393,663 A | 2/1995 | Patel et al. | |
| 5,523,223 A | 6/1996 | Kula et al. | |
| 6,218,156 B1 | 4/2001 | Hasegawa et al. | |
| 6,225,099 B1 | 5/2001 | Hummel et al. | |
| 6,255,087 B1 | 7/2001 | Dingler et al. | |
| 6,255,092 B1 | 7/2001 | Kojima et al. | |
| 6,416,986 B1 | 7/2002 | Kimoto et al. | |
| 6,645,746 B1 | 11/2003 | Hasegawa et al. | |
| 6,800,477 B2 | 10/2004 | Patel et al. | |
| 6,969,600 B2 | 11/2005 | Kimoto et al. | |
| 7,056,540 B2 | 6/2006 | Nanda et al. | |
| 7,083,962 B2 | 8/2006 | Kimoto et al. | |
| 7,172,894 B2 | 2/2007 | Itoh et al. | |
| 7,332,312 B2 | 2/2008 | Kizaki et al. | |
| 7,335,757 B2 | 2/2008 | Hiroaka et al. | |
| 7,371,903 B2 | 5/2008 | Gupta et al. | |
| 7,446,187 B2 | 11/2008 | Yamamura et al. | |
| 7,575,909 B2 | 8/2009 | Gupta et al. | |
| 7,598,279 B2 * | 10/2009 | Choi et al. ............ | 514/359 |
| 2002/0042110 A1 | 4/2002 | Kimoto et al. | |
| 2003/0032153 A1 | 2/2003 | Yamamoto et al. | |
| 2003/0054520 A1 | 3/2003 | Riebel et al. | |
| 2003/0130521 A1 | 7/2003 | Amano et al. | |
| 2004/0197773 A1 | 10/2004 | Kimoto et al. | |
| 2004/0265978 A1 | 12/2004 | Gupta et al. | |
| 2005/0003500 A1 | 1/2005 | Kudo et al. | |
| 2005/0202545 A1 | 9/2005 | Ishihara et al. | |
| 2005/0227336 A1 | 10/2005 | Yamamoto et al. | |
| 2006/0177913 A1 | 8/2006 | Peschko et al. | |
| 2006/0211099 A1 | 9/2006 | Althofer et al. | |
| 2006/0258718 A1 | 11/2006 | Choi et al. | |
| 2007/0212766 A1 | 9/2007 | Pfaller et al. | |
| 2008/0038803 A1 | 2/2008 | Hasegawa et al. | |
| 2008/0153140 A1 | 6/2008 | Gupta et al. | |
| 2008/0206824 A1 | 8/2008 | Streumer et al. | |
| 2008/0220484 A1 | 9/2008 | Breuer et al. | |
| 2008/0233621 A1 | 9/2008 | Dekishima et al. | |
| 2008/0261286 A1 | 10/2008 | Ishihara et al. | |
| 2009/0017510 A1 | 1/2009 | Gupta et al. | |
| 2009/0029430 A1 | 1/2009 | Kizaki et al. | |
| 2009/0148917 A1 | 6/2009 | Gupta et al. | |
| 2009/0162893 A1 | 6/2009 | Daussmann et al. | |
| 2009/0186391 A1 | 7/2009 | Nishiyama et al. | |
| 2009/0203096 A1 | 8/2009 | Hayashi et al. | |

FOREIGN PATENT DOCUMENTS

| | | |
|---|---|---|
| CA | 2625834 | 2/2007 |
| CA | 2621306 | 4/2007 |
| CA | 2633583 | 7/2007 |
| CA | 2671319 | 6/2008 |
| CN | 101314787 | 12/2008 |
| CN | 101319236 | 12/2008 |
| CN | 101358183 | 2/2009 |
| DE | 102004037669 | 3/2005 |
| DE | 102006055047 | 5/2008 |
| JP | 61134339 | 6/1986 |
| JP | 07059592 | 3/1995 |
| JP | 10094399 | 4/1998 |
| JP | 10248591 | 9/1998 |
| JP | 10287634 | 10/1998 |
| JP | 11130761 | 5/1999 |
| JP | 2003289895 | 10/2003 |
| JP | 2004267130 | 9/2004 |
| JP | 2004313033 | 11/2004 |
| JP | 2005006552 | 1/2005 |
| JP | 2007061065 | 3/2007 |
| JP | 2008017773 | 2/2008 |
| PL | 177372 | 11/1999 |
| WO | 9407888 | 4/1994 |
| WO | 2005049816 | 6/2005 |

(Continued)

OTHER PUBLICATIONS

The European Search Opinion mailed Oct. 22, 2012 from the European Patent Office in the corresponding European Patent Application No. 09846577.6.

(Continued)

*Primary Examiner* — Chih-Min Kam
(74) *Attorney, Agent, or Firm* — Harness, Dickey & Pierce, P.L.C.; J. Timothy Keane; Kisuk Lee

(57) ABSTRACT

Disclosed is a method for the preparation of carbamic acid (R)-1-aryl-2-tetrazolyl-ethyl ester, comprising the asymmetric reduction of arylketone and the carbamation of alcohol.

12 Claims, No Drawings

FOREIGN PATENT DOCUMENTS

| | | |
|---|---|---|
| WO | 2005108592 | 11/2005 |
| WO | 2006061137 | 6/2006 |
| WO | 2006094945 | 9/2006 |
| WO | 2006112685 | 10/2006 |
| WO | 2006130657 | 12/2006 |
| WO | 2007099764 | 9/2007 |
| WO | 2007099994 | 9/2007 |
| WO | 2008035187 | 3/2008 |
| WO | 2008064817 | 6/2008 |
| WO | 2008155302 | 12/2008 |
| WO | 2009040080 | 4/2009 |
| WO | 2009056614 | 5/2009 |
| WO | 2009070822 | 6/2009 |

OTHER PUBLICATIONS

D1: Hobub et al., "Catalytic enantioselective borane reduction of arylketones with pinene-derived amino alcohols," Tetrahedron, vol. 64, Issue 8, Feb. 18, 2008, pp. 1635-1640.

D2: Yadav et al., "A facile synthesis of (R)-(−)-2-azido-1-arylethanols from 2-azido-1-arylketones using baker's yeast," Tetrahedron: Asymmetry (Feb. 2001), 12 (1), p. 63-67.

The International Search Report and Written Opinion mailed on Apr. 28, 2010 in the corresponding PCT Application No. PCT/KR2009/005906.

The International Search Report and Written Opinion mailed on Jul. 11, 2011 in the related PCT Application No. PCT/KR2010/007069.

Rostom et al., "Azole antimicrobial pharmacophore-based tetrazoles: Synthesis and biological evaluation as potential antimicrobial and anticonvulsant agents," Bioorganic & Medicinal Chemistry 17 (2009) 2410-2422.

Office Actions mailed on Apr. 19, 2012, May 18, 2012 and Jan. 3, 2012, in related U.S. Appl. No. 12/904,267.

* cited by examiner

METHOD FOR PREPARATION OF CARBAMIC ACID (R)-1-ARYL-2-TETRAZOLYL-ETHYL ESTER

CROSS-REFERENCE TO RELATED APPLICATIONS

This application claims priority from Korean Patent Application No.: 10-2009-0055576 filed Jun. 22, 2009. The above mentioned application is incorporated herein by reference.

BACKGROUND OF THE INVENTION

1. Technical Field

The present invention relates to a method for the preparation of carbamic acid (R)-1-aryl-2-tetrazolyl-ethyl ester. More particularly, the present invention relates to a method for preparing carbamic acid (R)-1-aryl-2-tetrazolyl-ethyl ester, comprising the asymmetric reduction of an arylketone.

2. Description of the Related Art

As disclosed in U.S. Patent Application Publication No. 2006/0258718 A1, carbamic acid (R)-1-aryl-2-tetrazolyl-ethyl esters (hereinafter referred to as "the carbamate compounds") with anticonvulsant activity are useful in the treatment of disorders of the central nervous system, especially including anxiety, depression, convulsion, epilepsy, migraines, bipolar disorder, drug abuse, smoking, ADHD, obesity, sleep disorders, neuropathic pain, strokes, cognitive impairment, neurodegeneration, strokes and muscle spasms.

Depending on the position of N in the tetrazole moiety thereof, the carbamate compounds are divided into two positional isomers: tetrazole-1-yl (hereinafter referred to as "1N tetrazole") and treatzole-2-yl (hereinafter referred to as "2N tetrazole"). The introduction of tetrazole for the preparation of the carbamate compounds results in a 1:1 mixture of the two positional isomers which are required to be individually isolated for pharmaceutical use.

Having chirality, the carbamate compounds must be in high optical purity as well as chemical purity as they are used as medications.

In this regard, U.S. Patent Application Publication No. 2006/0258718 A1 uses the pure enantiomer (R)-aryl-oxirane as a starting material which is converted into an alcohol intermediate through a ring-opening reaction by tetrazole in the presence of a suitable base in a solvent, followed by introducing a carbamoyl group into the alcohol intermediate. For isolation and purification of the 1N and 2N positional isomers thus produced, column chromatography is set after the formation of an alcohol intermediate or carbamate.

For use in the preparation, (R)-2-aryl-oxirane may be synthesized from an optically active material, such as substituted (R)-mandelic acid derivative, via various routes or obtained by asymmetric reduction-ring formation reaction of a-halo arylketone or by separation of racemic 2-aryl-oxirane mixture into its individual enantiomers. As such, (R)-2-aryl-oxirane is an expensive compound.

In addition, the ring-opening reaction of (R)-2-aryl-oxirane with tetrazole is performed at relatively high temperatures because of the low nucleophilicity of the tetrazole. However, the ring opening reaction includes highly likely risk of a runaway reaction because tetrazoles start to spontaneously degrade at 110~120° C.

In terms of a selection of reaction, as there are two reaction sites in each (R)-2-aryl-oxirane and tetrazole, the ring-opening reaction therebetween affords the substitution of 1N- or 2N-tetrazole at the benzyl or terminal position, resulting in a mixture of a total of 4 positional isomers. Therefore, individual positional isomers are low in production yield and difficult to isolate and purify.

SUMMARY OF THE INVENTION

Accordingly, the present invention has been made keeping in mind the above problems occurring in the prior art, and an object of the present invention is to provide a novel method for preparing novel (R)-1-aryl-2-tetrazolyl-ethyl ester.

In order to accomplish the above object, the present invention provides a method for preparing carbamic acid (R)-1-aryl-2-tetrazolyl ethyl ester, represented by Chemical Formula 1, comprising: subjecting an arylketone, represented by Chemical Formula 2, to (R)-selective asymmetric reduction to form an alcohol compound of (R)-configuration, represented by Chemical Formula 3; and carbamating said alcohol:

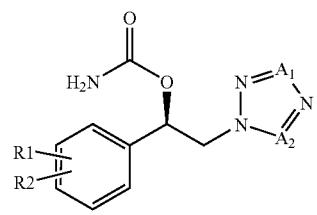

[Chemical Formula 1]

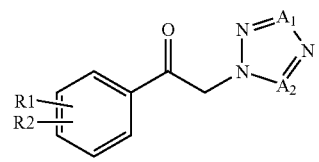

[Chemical Formula 2]

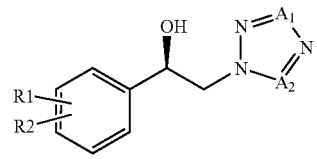

[Chemical Formula 3]

wherein, $R_1$ and $R_2$ are independently selected from a group consisting of hydrogen, halogen, perfluoroalkyl, alkyl of 1 to 8 carbon atoms, thioalkoxy of 1 to 8 carbon atoms, and alkoxy of 1 to 8 carbon atoms; and one of $A_1$ and $A_2$ is CH with the other being N.

DESCRIPTION OF THE PREFERRED EMBODIMENTS

In accordance with an embodiment of the present invention, a method comprising (R)-selective asymmetric reduction of an arylketone represented by the following Chemical Formula 2 and the carbamation of an alcohol compound represented by the following Chemical Formula 3 is provided for the preparation of carbamic acid (R)-1-aryl-2-tetrazolyl-ethyl ester, represented by the following Chemical Formula 1.

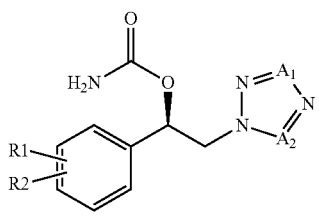

[Chemical Formula 1]

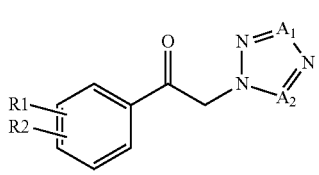

[Chemical Formula 2]

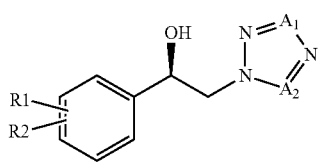

[Chemical Formula 3]

wherein, $R_1$ and $R_2$ are independently selected from a group consisting of hydrogen, halogen, perfluoroalkyl, alkyl of 1 to 8 carbon atoms, thioalkoxy of 1 to 8 carbon atoms, and alkoxy of 1 to 8 carbon atoms; and one of $A_1$ and $A_2$ is CH with the other being N.

The arylketone of Chemical Formula 2, useful as a starting material in the preparation method of the present invention, may be synthesized by, for example, a substitution reaction between the arylketone of Chemical Formula 4 and the tetrazole of Chemical Formula 5:

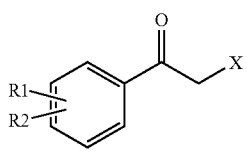

[Chemical Formula 4]

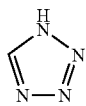

[Chemical Formula 5]

wherein, $R_1$ and $R_2$ are as defined above; and

X is a leaving group such as a halide or sulfonate.

An economical advantage is given to the synthesis of the arylketone of Chemical Formula 2 from the compounds represented by Chemical Formulas 4 and 5 because they are commercially available, cheap compounds. In addition, the substitution reaction can be carried out in relatively mild conditions, compared to the ring-opening reaction between (R)-2-aryl-oxirane and tetrazole. The method according to the present invention is therefore certain of process safety although employing potentially explosive tetrazole, and ensures high production yield and easy purification, with the production of no unnecessary positional isomers at benzyl positions.

The arylketone represented by Chemical Formula 2 which can be synthesized by the substitution reaction with tetrazole may be in a mixture of positional isomers including 1N arylketone of the following Chemical Formula 2a and 2N arylketone of the following Chemical Formula 2b, which can be isolated and purified through commercially available crystallization.

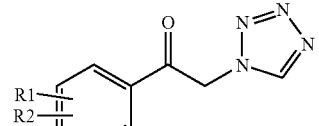

[Chemical Formula 2a]

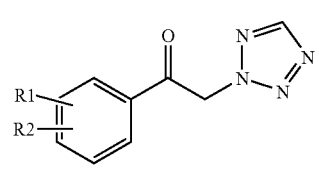

[Chemical Formula 2b]

The crystallization useful in the present invention may comprise adding a solubilizing agent to the product of the substitution reaction, that is, a mixture of the positional isomers, and then adding a precipitating agent. Optionally, the crystallization may further comprise, after the precipitation, filtrating the precipitate, concentrating the filtrate and adding an additional precipitating agent.

Illustrative, non-limiting examples of the solubilizing agent include acetone, acetonitrile, tetrahydrofuran, ethylacetate, dichloromethane, chloroform, 1,4-dioxane, and lower alcohols of 1 to 4 carbon atoms, and a combination thereof. The solubilizing agent may be used in an amount of from 0 to 20 ml (v/w) based on the weight (g) of the mixture of the positional isomers. As used herein, the addition of the solubilizing agent in an amount of zero ml (v/w) is intended to mean immediately adding the subsequent additive without dilution of the filtrate.

Examples of the precipitating agent include water, C1-C4 lower alcohol, diethylether, pentane, hexane, cyclohexane, heptane and a combination thereof, but are not limited thereto. The precipitating agent may be slowly added in an amount of from zero to 40 ml (v/w) based on the weight (g) of the mixture of positional isomers. As used herein, the addition of the precipitating agent in an amount of zero ml is intended to mean leaving or cooling to yield precipitates without the addition of the precipitating agent.

The filtration of the precipitates thus obtained by the addition of the precipitating agent yields the 1N arylketone of Chemical Formula 2a as a crystal with high purity.

On the other hand, the filtrate thus obtained after the filtration step may be concentrated to increase the ratio of the precipitating agent to the solubilizing agent, thereby yielding the 2N arylketone of Chemical Formula 2b with high purity. Concentration ratio of the filtrate can be suitably determined by those of ordinary skill in the art. For example, concentration is carried until the solvent is totally removed off, then the solubilizing agent and the precipitating agent are added as mentioned above.

Unlike column chromatography, this crystallization may be commercially used without much difficulty.

(R)-Selective asymmetric reduction allows for the conversion of the arylketone of Chemical Formula 2 into the alcohol compound with (R)-configuration, represented by the following Chemical Formula 3.

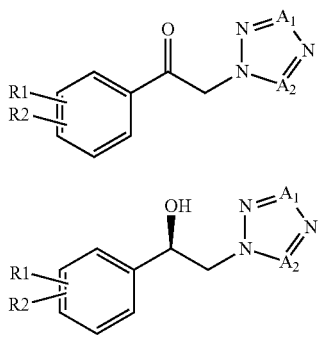

[Chemical Formula 2]

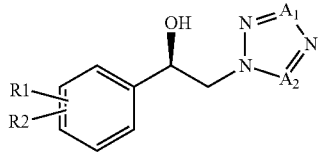

[Chemical Formula 3]

wherein, $R_1$ and $R_2$ are independently selected from a group consisting of hydrogen, halogen, perfluoroalkyl, an alkyl of 1 to 8 carbon atoms, a thioalkoxy of 1 to 8 carbon atoms, and alkoxy of 1 to 8 carbon atoms; and one of $A_1$ and $A_2$ is CH with the other being N.

The (R)-selective asymmetric reduction can be achieved, for example, biologically or chemically.

In the method for preparing carbamic acid (R)-1-aryl-2-tetrazolyl-ethyl ester according to an embodiment of the present invention, the arylketone compound of Chemical Formula 2 is converted into an alcohol compound with (R)-configuration of optically high purity by biological asymmetric reduction.

The biological asymmetric reduction can be achieved in a buffer containing a microbial strain capable of producing oxidoreductase, the arylketone compound of Chemical Formula 2 and a cosubstrate at an appropriate temperature. Examples of the microbial strain capable of producing oxidoreductase include yeast of the *Candida* genus, such as *Candida parapsilosis* or *Candida rugosa*; yeast of the *Pichia* genus, such as *Pichia anomala* or *Pichia jadinii*; yeast of the *Saccharomyces* genus, such as Baker's yeast, *Saccharomyces cerevisiae* or *Saccharomyces pastorianus*; other yeast such as *Rhodotorula mucilaginosa* or *Trigonopsis variabilis*; bacteria, such as *Klebsiella pneumoniae, Enterobacter cloacae, Erwinia herbicola, Micrococcus luteus, Bacillus stearothermophilus, Rhodococcus erythropolis* or *Rhodococcus rhodochrous*; fungi, such as *Mucor racemosus* or *Geotrichum candidum*, etc.

The microbial strain capable of producing oxidoreductase may be used in an amount of from about 0.1 to 10 g per gram of the arylketone of Chemical Formula 2.

To enhance the rate of the biological asymmetric reduction, an additional coenzyme such as nicotineamide adenine dinucleotide phosphate (NADP) or nicotineamide adenine dinucleotide (NAD) may be added to the buffer with a use amount from about 0.1 to 1 mg per gram of the arylketone of Chemical Formula 2.

The coenzyme, NADP or NAD may be converted to its reduced form, NADPH or NADH, respectively with the aid of the oxidoreductase and/or a cosubstrate.

Examples of the cosubstrate include saccharides such a glucose, glycerol or sucrose; and alcohols such as methanol, ethanol, 1-propanol, isopropanol, 1-butanol, 2-butanol, 2-pentanol, 2-methylpentanol, 2-hexanol, 2-heptanol, 2-octanol, cyclopentanol, cyclohexanol, 2-methyl 2-butanol, etc. Among the alcohols mentioned beforehand, methanol, 1-propanol, 1-butanol and 2-methyl 2-butanol are preferable.

The buffer useful in the biological asymmetric reduction may be PBS (phosphate buffered saline) or a solution of sodium phosphate, potassium phosphate or triethanolamine in water, for example, at a pH of 6 to 8.

The biological asymmetric reduction may be carried out at from 10 to 45° C.

In addition to being economical and environment-friendly, the biological selective reduction allows for very high enantioselectivity. Thus, an alcohol compound with an (R)-configuration of high optical purity can be obtained in the presence of the enzyme under the above-mentioned reaction conditions.

In the method for preparing carbamic acid (R)-1-aryl-2-tetrazolyl-ethyl ester according to another embodiment of the present invention, the arylketone compound of Chemical Formula 2 is chemically converted into an alcohol compound with (R)-configuration of high optical purity under asymmetric conditions.

Chemical asymmetric reduction may be accomplished, for example, with a chiral borane reductant at an appropriate temperature in an organic solvent, or by asymmetric catalytic hydrogenation or asymmetric catalytic transfer hydrogenation.

As concerns the use of a chiral borane reductant, 1 to 4 equivalents of sodium (−)-B-chlorodiisopinochampheylborane (hereinafter referred to as "(−)-DIP-Cl") or (R)-2-methyl-CBS-oxazaborolidine/borane (hereinafter referred to as "(R)-CBS/BH$_3$") are added to a solution of the arylketone compound of Chemical Formula 2 in an organic solvent such as diethylether, tetrahydrofuran, 1,4-dioxane, acetonitrile, dichloromethane, chloroform or a mixture thereof, and the reaction may be conducted at about −10 to about 60° C.

The asymmetric catalytic hydrogenation may be conducted as follows: the 0.0004 to 0.2 equivalents of an inorganic base may be added to the solution with 0.0002 to 0.1 equivalents of (R)-bisphosphono-ruthenium (II)-(R,R)-chiral diamine complex catalyst dissolved in organic solvent such as isopropanol, methanol, ethanol or t-butylalcohol. The arylketone compound of Chemical formula 2 may be added and the resultant solution may hold at about −10 to about 60° C. under hydrogen pressure of 1 to 20 atm. A non-limiting example of the catalyst useful in the asymmetric catalytic hydrogenation is dichloro[(R)-(+)-2,2'-bis(diphenylphosphono)1,1'-binaphthyl][(1R,2R)-(+)-1,2-diphenylethylenediamine]ruthenium (II) represented by the following Chemical Formula 6.

[Chemical Formula 6]

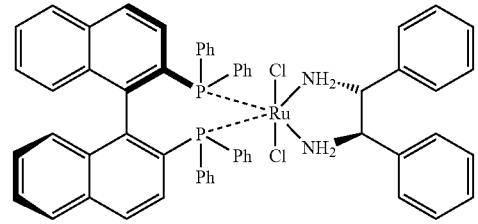

Turning to the asymmetric catalytic transfer hydrogenation, it may be carried out by adding 0.001~0.1 equivalents of [S,S]-monosulfonatediamine-M(II) arene complex catalyst (wherein M is ruthenium or rhodium) to a solution of the arylketone compound of Chemical Formula 2 in 5:2 formic acid-triethylamine azeotrope or isopropanol at about −10 to 60° C. A non-limiting example of catalyst useful for the asymmetric catalytic transfer hydrogenation may be chloro{[(1S,2S)-(+)-amino-1,2-diphenylethyl](4-toluenesulfonyl)amido}(p-cymene)ruthenium(II), represented by the following Chemical Formula 7.

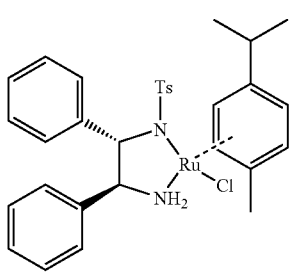

[Chemical Formula 7]

The alcohol compound obtained through the asymmetric reduction may exist as a positional isomer mixture of 1N alcohol of Chemical Formula 3a and 2N alcohol of Chemical Formula 3b that can be isolated and purified into individual positional isomers of high purity by crystallization:

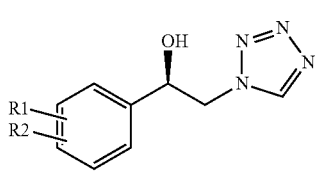

[Chemical Formula 3a]

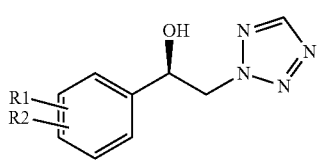

[Chemical Formula 3b]

The crystallization may comprise adding a solubilizing agent to the positional isomer mixture resulting from the asymmetric reduction; and adding a precipitating agent, and optionally filtering the precipitate; and concentrating the filtrate and adding an additional precipitating agent.

Examples of the solubilizing agent useful in the crystallization include acetone, acetonitrile, tetrahydrofuran, ethylacetate, dichloromethane, chloroform, 1,4-dioxane, lower alcohol of 1 to 4 carbon atoms, and a mixture thereof, but are not limited thereto. The solubilizing agent may be added in an amount of zero to 20 ml (v/w) based on the weight (g) of the positional isomer mixture.

Non-limiting examples of the precipitating agent include water, a lower alcohol of 1 to 4 carbon atoms, diethylether, pentane, hexane, cyclohexane, heptane, and a mixture thereof. The precipitating agent may be slowly added in an amount of from zero to 40 ml (v/w) based on the weight (g) of the positional isomer mixture.

Following the addition of the precipitating agent, filtration may yield 1N alcohol (3a) as a precipitate of high purity.

Furthermore, 2N alcohol (3b) can be obtained as a crystal form of very high purity by concentrating the filtrate and increasing the ratio of the precipitating agent to the solubilizing agent.

These crystallization steps may be omitted when the positional isomers of arylketone of Chemical Formula 2 are already isolated and purified.

The introduction of a carbomoyl moiety into the alcohol compound with (R)-configuration of Chemical Formula 3 leads to carbamate with (R)-configuration, represented by Chemical Formula 1:

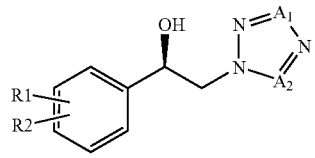

[Chemical Formula 3]

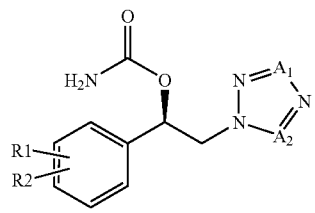

[Chemical Formula 1]

wherein, $R_1$ and $R_2$ are independently selected from a group consisting of hydrogen, halogen, perfluoroalkyl, an alkyl of 1 to 8 carbon atoms, a thioalkoxy of 1 to 8 carbon atoms, and an alkoxy of 1 to 8 carbon atoms; and one of $A_1$ and $A_2$ is CH with the other being N.

In the carbamation step, for example, inorganic cyanate-organic acid, isocyanate-water, or carbonyl compound-ammonia may be employed to introduce a carbamoyl moiety.

For the carbamation with inorganic cyanate-organic acid, the alcohol compound with (R)-configuration of Chemical Formula 3 is dissolved in an organic solvent, for example, diethylether, tetrahydrofuran, 1,4-dioxane, acetonitrile, dichloromethane, chloroform or a mixture thereof, and mixed with 1 to 4 equivalents of inorganic cyanate such as sodium cyanate and organic acid, such as methane sulfonic acid or acetic acid, followed by reacting at about −10 to 70° C.

With regard to use of the isocyanate-water, 1 to 4 equivalents of isocyanate, for example, chlorosulfonic isocyanate, trichloroacetyl isocyanate, trimethylsilyl isocyanate, are added to a solution of the alcohol compound with (R)-configuration of Chemical Formula 3 in an organic solvent, for example, diethylether, tetrahydrofuran, 1,4-dioxane, acetonitrile, dichloromethane, chloroform or a mixture thereof, and reacted at about −50 to 40° C. Subsequently, without purification, 1 to 20 equivalents of water were added to induce hydrolysis.

With regard to use of the carbonyl compound-ammonia, 1 to 4 equivalents of a carbonyl compound, for example, 1,1'-carbonyldiimidazole, carbamoly chloride, N,N'-disuccinmidyl carbonate, phosgene, triphosgene, or chloroformate, are added to a solution of the alcohol compound with (R)-configuration of Chemical Formula 3 in an organic solvent, for example, diethylether, tetrahydrofuran, 1,4-dioxane, acetonitrile, dichloromethane, chloroform or a mixture thereof, and reacted at about −10 to 70° C., followed by adding 1 to 10 equivalents of ammonia without purification.

After the carbamation, the carbamate compound of Chemical Formula 1 thus obtained may be purified to higher optical and chemical purity through the following crystallization. The crystallization comprises adding a solubilizing agent to the product of the carbamation; and then adding a precipitating agent, and optionally filtering the precipitate and adding an additional precipitating agent. For pharmaceutical use, it is preferable that there is always a final purification of the carbamated product before use, but that there can be a crystallization step earlier in the process.

Non-limiting examples of the solubilizing agent include acetone, acetonitrile, tetrahydrofuran, ethylacetate, dichloromethane, chloroform, 1,4-dioxane, lower alcohol of 1 to 4 carbon atoms, and a mixture thereof Based on the weight (g) of the reaction product, the solubilizing agent may be used in an amount of from zero to 20 ml (v/w).

Non-limiting examples of the precipitating agent include water, lower alcohols of 1 to 4 carbon atoms, diethylether, pentane, hexane, cyclohexane, heptane and a mixture thereof. Based on the weight (g) of the reaction product, the precipitating agent may be slowly added in an amount of from zero to 40 ml (v/w). Comprising biological or chemical asymmetric reduction, the method of the present invention can provide optically high pure carbamate compounds. In addition, the mild reaction conditions which the method of the present invention requires ensure process safety. Furthermore, the crystallization step applicable to large-scale production before or after the asymmetric reduction or after the carbamation results in a higher chemical purity of the carbamate compounds.

As demonstrated in the following examples, the carbamate compounds prepared according to the present invention are very useful in the treatment of CNS disorders such as convulsion.

A better understanding of the present invention may be obtained through the following examples which are set forth to illustrate, but are not to be construed as limiting the present invention.

EXAMPLES

Preparation of Tetrazole Arylketones

Preparation Example 1

Preparation of 1-(2-chlorophenyl)-2-(1,2,3,4-tetrazol-1-yl)ethan-1-one

To a suspension of 2-bromo-2'-chloroacetophenone (228.3 g, 0.978 mol) and potassium carbonate (161.6 g, 1.170 mol) in acetonitrile (2000 mL) was added a 35 w/w % 1H-tetrazole dimethylformamide solution (215.1 g, 1.080 mol) at room temperature. These reactants were stirred for 2 h at 45° C. and distilled under reduced pressure to remove about 1500 mL of the solvent. The concentrate was diluted in ethylacetate (2000 mL) and washed with 10% brine (3×2000 mL) The organic layer thus separated was distilled under reduced pressure to afford 216.4 g of an oily solid residue. To a solution of the solid residue in ethylacetate (432 mL) was slowly added heptane (600 mL). The precipitate thus formed was filtered at room temperature and washed to yield 90.1 g (0.405 mol) of 1-(2-chlorophenyl)-2-(1,2,3,4-tetrazol-1-yl)ethan-1-one (hereinafter referred to as "1N ketone").

$^1$H-NMR(CDCl$_3$) δ8.87(s, 1H), d7.77(d, 1H), d7.39-7.62 (m, 3H), d5.98(s, 2H)

Preparation Example 2

Preparation of 1-(2-chlorophenyl)-2-(1,2,3,4-tetrazol-2-yl)ethan-1-one

After the filtration of Preparation Example 1, the filtrate was concentrated and dissolved in isopropanol (100 mL), and to which heptane (400 mL) was then added to complete the crystallization. Filtering and washing at 5° C. afforded 1-(2-chlorophenyl)-2-(1,2,3,4-tetrazol-2-yl)ethan-1-one (hereinafter referred to as "2N ketone") as a solid. 94.7 g (0.425 mol).

$^1$H-NMR(CDCl$_3$) d8.62(s, 1H), d7.72(d, 1H), d7.35-7.55 (m, 3H), d6.17(s, 2H)

Preparation of Alcohol Compound of (R)-Configuration by Biological Asymmetric Reduction Suitable for use in the biological asymmetric reduction is a strain expressing oxidoreductase. Like baker's yeast (Jenico), a strain commercially available in a freeze-dried form may be weighed properly for the reaction. As like other micorbial strans, the strain stored in a deep freezer (Revco) may be spread on LB plates medium (Bactotrypton: 1%, yeast extract: 0.5%, NaCl: 0.5%, glucose: 0.1%, agar: 1.5%) to form colonies. The one of which is then inoculated into 3 mL of an LB medium in a tube and pre-incubated at 30° C. for 1 day. After completion of the pre-incubation, it was scaled up to 300 mL of LB medium in 1 L Erlenmeyer flask, followed by incubation at 30° C. for 2 days. Centrifugation precipitates the strain into a pellet which is quantified for use in the reaction.

Preparation Example 3

Preparation of 1N Alcohol with *Rhodotorula mucilaginosa*

1-(2-Chlorophenyl)-2-(1,2,3,4-tetrazol-1-yl)ethan-1-one (100 mg, 0.449 mmol), prepared in Preparation Example 1, was incubated at room temperature for 4 days with nicotinamide adenine dinucleotide (NAD, 0.5 mg) in the presence of *Rhodotorula mucilaginosa* KCTC7117 (500 mg), a microbial strain producing oxidoreductase, in PBS (10 mL, pH7.0) containing 5% (w/v) glycerol, after which extraction with ethylacetate (1 mL) gave an alcohol of R-configuration, that is, (R)-1-(2-chlorophenyl)-2-(1,2,3,4-tetrazol-1-yl)ethan-1-ol (hereinafter referred to as "1N alcohol"). Conversion rates and optical purities of products are listed in Table 1, below. Conversion rates (%), purities (%) and optical purifies of products were measured using HPLC and calculated using the following equations.

Conversion Rate (%)=[(Area of Product)/(Area of Reactant+Area of Product)]×100

Purity (%)=(Area of Product)/(Area of All Peaks on HPLC)]×100

Optical Purity (%)=[(Area of R-Configuration−Area of S-Configuration)/(Area of R-Configuration+ Area of S-Configuration)]×100

$^1$H-NMR(CDCl$_3$) d8.74(s, 1H), d7.21-7.63(m, 4H), d5.57 (m, 1H), d4.90(d, 1H), d4.50(d, 1H), d3.18(d, 1H)

Preparation Example 4

Preparation of 2N Alcohol with *Rhodotorula mucilaginosa*

The same procedure as in Preparation Example 3 was repeated, with the exception that 1-(2-chlorophenyl)-2-(1,2,3,4-tetrazol-2-yl)ethan-1-one, prepared in Preparation Example 2, was used instead of 1-(2-chlorophenyl)-2-(1,2,3,4-tetrazol-1-yl)ethan-1-one, to afford (R)-1-(2-chlorophenyl)-2-(1,2,3,4-tetrazol-2-yl)ethan-1-ol (hereinafter referred to as "2N alcohol"). The conversion rate and optical purity of the product are given in Table 1, below.

$^1$H-NMR(CDCl$_3$) d8.55(s, 1H), d7.28-7.66(m, 4H), d5.73 (d, 1H), d4.98(d, 1H), d4.83(d, 1H), d3.38(br, 1H)

Preparation Example 5

Preparation of 1N Alcohol with *Trigonopsis variabilis*

The same procedure as in Preparation Example 3 was repeated, with the exception that *Trigonopsis variabilis* KCTC7263 was used as a strain producing an oxidoreductase, instead of *Rhodotorula mucilaginosa* KCTC7117, to afford 1N alcohol of R-configuration. Its conversion rate and optical purity are given in Table 1, below.

Preparation Example 6

Preparation of 2N Alcohol with *Trigonopsis variabilis*

The same procedure as in Preparation Example 4 was repeated, with the exception that *Trigonopsis variabilis* KCTC7263 was used as a strain producing an oxidoreductase, instead of *Rhodotorula mucilaginosa* KCTC7117, to afford 2N alcohol of R-configuration. Its conversion rate and optical purity are given in Table 1, below.

TABLE 1

| Example No. | Strain | Product | Conversion Rate [%] | Optical Purity [%] |
|---|---|---|---|---|
| 3 | Rhodotorula mucilaginosa KCTC 7117 | 1N Alcohol | 54.1 | 98.9 |
| 4 | Rhodotorula mucilaginosa KCTC 7117 | 2N Alcohol | 78.5 | 97.4 |
| 5 | Trigonopsis variabilis KCTC 7263 | 1N Alcohol | 11.9 | 99.9 |
| 6 | Trigonopsis variabilis KCTC 7263 | 2N Alcohol | 28.3 | 99.9 |

Preparation Examples 7 and 8

Preparation of 1N Alcohol with Yeasts of *Candida* Genus

The same procedure as in Preparation Example 3 was repeated, with the exception that *Candida parapsilosis* ATCC20179 or *Candida rugosa* KCTC7292 was used as a strain producing an oxidoreductase, instead of *Rhodotorula mucilaginosa* KCTC7117, to afford 1N alcohol of R-configuration. Its conversion rate and optical purity are given in Table 2, below.

Preparation Examples 9 and 10

Preparation of 2N Alcohol with Yeasts of *Candida* Genus

The same procedure as in Preparation Example 4 was repeated, with the exception that *Candida parapsilosis* ATCC20179 or *Candida rugosa* KCTC7292 was used as a strain producing an oxidoreductase, instead of *Rhodotorula mucilaginosa* KCTC7117, to afford 2N alcohol of R-configuration. Its conversion rate and optical purity are given in Table 2, below.

TABLE 2

| Example No. | Strain | Product | Conversion Rate [%] | Optical Purity [%] |
|---|---|---|---|---|
| 7 | Candida parapsilosis ATCC 20179 | 1N Alcohol | 46.5 | 98.5 |
| 8 | Candida rugosa KCTC 7292 | 1N Alcohol | 27.6 | 99 |
| 9 | Candida parapsilosis ATCC 20179 | 2N Alcohol | 70.1 | 97.9 |
| 10 | Candida rugosa KCTC 7292 | 2N Alcohol | 65.4 | 99 |

Preparation Examples 11 and 12

Preparation of 1N Alcohol with Yeasts of *Pichia* Genus

The same procedure as in Preparation Example 3 was repeated, with the exception that *Pichia anomala* KCTC 1206 or *Pichia jadinii* KCTC7008 was used as a strain producing an oxidoreductase, instead of *Rhodotorula mucilaginosa* KCTC7117, to afford 1N alcohol of R-configuration. Its conversion rate and optical purity are given in Table 3, below.

Preparation Examples 13 and 14

Preparation of 2N Alcohol with Yeasts of *Pichia* Genus

The same procedure as in Preparation Example 4 was repeated, with the exception that *Pichia anomala* KCTC 1206 or *Pichia jadinii* KCTC7008 was used as a strain producing an oxidoreductase, instead of *Rhodotorula mucilaginosa* KCTC7117, to afford 2N alcohol of R-configuration. Its conversion rate and optical purity are given in Table 3, below.

TABLE 3

| Example No. | Strain | Product | Conversion Rate [%] | Optical Purity [%] |
|---|---|---|---|---|
| 11 | *Pichia anomala* KCTC 1206 | 1N Alcohol | 23.8 | 99.9 |
| 12 | *Pichia jadinii* KCTC 7008 | 1N Alcohol | 56.1 | 99.9 |

TABLE 3-continued

| Example No. | Strain | Product | Conversion Rate [%] | Optical Purity [%] |
|---|---|---|---|---|
| 13 | *Pichia anomala* KCTC 1206 | 2N Alcohol | 53.8 | 98.2 |
| 14 | *Pichia jadinii* KCTC 7008 | 2N Alcohol | 78.3 | 98.9 |

Preparation Examples 15 to 20

Preparation of 1N Alcohol with Yeast of *Saccharomyces* Genus

The same procedure as in Preparation Example 4 was repeated, with the exception that Baker's yeast, *Saccharomyces cerevisiae* KCTC7108, *Saccharomyces cerevisiae* KCTC1205, *Saccharomyces cerevisiae* KCTC7107, *Saccharomyces cerevisiae* KCTC1552 or *Saccharomyces pastorianus* KCTC1218 was used as a strain producing an oxidoreductase, instead of *Rhodotorula mucilaginosa* KCTC7117, to afford 1N alcohol of R-configuration. Its conversion rate and optical purity are given in Table 4, below.

Preparation Example 21 to 26

Preparation of 2N Alcohol with Yeasts of *Saccharomyces* Genus

The same procedure as in Preparation Example 4 was repeated, with the exception that Baker's yeast, *Saccharomyces cerevisiae* KCTC7108, *Saccharomyces cerevisiae* KCTC1205, *Saccharomyces cerevisiae* KCTC7107, *Saccharomyces cerevisiae* KCTC1552 or *Saccharomyces pastorianus* KCTC1218 was used as a strain producing an oxidoreductase, instead of *Rhodotorula mucilaginosa* KCTC7117, to afford 2N alcohol of R-configuration. Its conversion rate and optical purity are given in Table 4, below.

TABLE 4

| Example No. | Strain | Product | Conversion Rate [%] | Optical Purity [%] |
|---|---|---|---|---|
| 15 | Baker's yeast | 1N Alcohol | 74.6 | 99.9 |
| 16 | *Saccharomyces cerevisiae* KCTC 7108 | 1N Alcohol | 32.7 | 93.8 |
| 17 | *Saccharomyces cerevisiae* KCTC 1205 | 1N Alcohol | 36.6 | 89.9 |
| 18 | *Saccharomyces cerevisiae* KCTC7107 | 1N Alcohol | 18.2 | 94.6 |
| 19 | *Saccharomyces cerevisiae* KCTC 1552 | 1N Alcohol | 19.8 | 91.8 |
| 20 | *Saccharomyces pastorianus* KCTC 1218 | 1N Alcohol | 20.4 | 92.5 |
| 21 | Baker's yeast | 2N Alcohol | 85.1 | 98.1 |
| 22 | *Saccharomyces cerevisiae* KCTC 7108 | 2N Alcohol | 57.4 | 90.5 |
| 23 | *Saccharomyces cerevisiae* KCTC 1205 | 2N Alcohol | 64.8 | 86.5 |
| 24 | *Saccharomyces cerevisiae* KCTC7107 | 2N Alcohol | 36 | 87.7 |
| 25 | *Saccharomyces cerevisiae* KCTC 1552 | 2N Alcohol | 38.5 | 83.3 |
| 26 | *Saccharomyces pastorianus* KCTC 1218 | 2N Alcohol | 33.8 | 77.2 |

Preparation Examples 27 to 30

Preparation of 1N Alcohol with Bacteria

The same procedure as in Preparation Example 3 was repeated, with the exception that *Klebsiella pneumoniae* IFO3319, *Bacillus stearothermophilus* KCTC1752, *Rhodococcus erythropolis* KCCM40452 or *Rhodococcus rhodochrous* ATCC21197 was used as a strain producing an oxidoreductase, instead of *Rhodotorula mucilaginosa* KCTC7117, to afford 1N alcohol of R-configuration. Their conversion rates and optical purities are given in Table 5, below.

Preparation Examples 31 to 37

Preparation of 2N Alcohol with Bacteria

The same procedure as in Preparation Example 4 was repeated, with the exception that *Klebsiella pneumoniae* IFO3319, *Enterobacter cloacae* KCTC2361, *Erwinia herbicola* KCTC2104, *Micrococcus luteus* KCTC1071, *Bacillus stearothermophilus* KCTC1752, *Rhodococcus erythropolis* KCCM40452 or *Rhodococcus rhodochrous* ATCC21197 was used as a strain producing an oxidoreductase, instead of *Rhodotorula mucilaginosa* KCTC7117, to afford 2N alcohol of R-configuration. Their conversion rates and optical purities are given in Table 5, below.

TABLE 5

| Example No. | Strain | Product | Conversion Rate [%] | Optical Purity [%] |
|---|---|---|---|---|
| 27 | Klebsiella pneumonia IFO 3319 | 1N Alcohol | 1.3 | 99.9 |
| 28 | Bacillus stearothermophilus KCTC 1752 | 1N Alcohol | 14 | 94.9 |
| 29 | Rhodococcus erythropolis KCCM 40452 | 1N Alcohol | 42 | 90.1 |
| 30 | Rhodococcus rhodochrous ATCC 21197 | 1N Alcohol | 14.1 | 92.9 |
| 31 | Klebsiella pneumonia IFO 3319 | 2N Alcohol | 3.4 | 99.9 |
| 32 | Enterobacter cloacae KCTC 2361 | 2N Alcohol | 11.8 | 89.2 |
| 33 | Erwinia herbicola KCTC 2104 | 2N Alcohol | 6 | 87.7 |
| 34 | Micrococcus luteus KCTC1071 | 2N Alcohol | 13.3 | 92.6 |
| 35 | Bacillus stearothermophilus KCTC 1752 | 2N Alcohol | 40.1 | 88.2 |
| 36 | Rhodococcus erythropolis KCCM 40452 | 2N Alcohol | 69.8 | 80.6 |
| 37 | Rhodococcus rhodochrous ATCC 21197 | 2N Alcohol | 25.4 | 74.8 |

Preparation Examples 38 and 39

Preparation of 1N Alcohol with Fungi

The same procedure as in Preparation Example 3 was repeated, with the exception that *Mucor racemosus* KCTC6119, *Geotrichum candidum* KCTC6195, *Geotrichum candidum* IFO5767 or *Geotrichum candidum* IFO4597 was used as a strain producing an oxidoreductase, instead of *Rhodotorula mucilaginosa* KCTC7117, to afford 1N alcohol of R-configuration. Their conversion rates and optical purities are given in Table 6, below.

Preparation Examples 40 to 42

Preparation of 2N Alcohol with Fungi

The same procedure as in Preparation Example 4 was repeated, with the exception that *Mucor racemosus* KCTC6119, *Geotrichum candidum* KCTC6195, *Geotrichum candidum* IFO5767 or *Geotrichum candidum* IFO4597 was used as a strain producing an oxidoreductase, instead of *Rhodotorula mucilaginosa* KCTC7117, to afford 2N alcohol of R-configuration. Their conversion rates and optical purities are given in Table 6, below.

TABLE 6

| Example No. | Strain | Product | Conversion Rate [%] | Optical Purity [%] |
|---|---|---|---|---|
| 38 | Mucor racemosus KCTC 6119 | 1N Alcohol | 10.2 | 97.1 |
| 39 | Geotrichum candidum IFO 4597 | 1N Alcohol | 18.2 | 99.9 |
| 40 | Mucor racemosus KCTC 6119 | 2N Alcohol | 32.7 | 95.1 |
| 41 | Geotrichum candidum KCTC 6195 | 2N Alcohol | 25.3 | 96.3 |
| 42 | Geotrichum candidum IFO 4597 | 2N Alcohol | 32 | 96.3 |

Preparation of Alcohol Compound of (R)-Configuration by Chemical Asymmetric Reduction Preparation Examples 43 and 44

Preparation of 1N Alcohol with Chiral Borane Reductant

To a solution of 1N ketone (100 mg, 0.449 mmol), prepared in Preparation Example 1, in tetrahydrofuran (1 mL) was added 2 equivalents of a chiral borane reductant, such as (−)-B-chlorodiisopinocampheylborane or (R)-2-methyl-CBS-oxazaborolidine/borane, at 0° C. Stirring at room temperature for 24 h was followed by extraction with ethyl acetate (1 mL) to give the results of Table 7, below.

Preparation Examples 45 and 46

Preparation of 2N Alcohol with Chiral Borane Reductant

To a solution of 2N ketone (100 mg, 0.449 mmol), prepared in Preparation Example 2, in tetrahydrofuran (1 mL) was added 2 equivalents of a chiral borane reductant, such as (−)-B-chlorodiisopinocampheylborane or (R)-2-methyl-CBS-oxazaborolidine/borane, at 0° C. Stirring at room temperature for 24 h was followed by extraction with ethyl acetate (1 mL) to give the results of Table 7, below.

TABLE 7

| Example No. | Chiral Borane Reductant | Product | Conversion Rate [%] | Optical Purity [%] |
|---|---|---|---|---|
| 43 | (−)-B-chlorodiisopinocampheylborane | 1N Alcohol | 99.0 | 83.0 |
| 44 | (R)-2-methyl-CBS-oxazaborolidine/borane | 1N Alcohol | 99.0 | 14.1 |
| 45 | (−)-B-chlorodiisopinocampheylborane | 2N Alcohol | 99.0 | 84.6 |
| 46 | (R)-2-methyl-CBS-oxazaborolidine/borane | 2N Alcohol | 99.0 | 31.5 |

Preparation Examples 47 and 48

Preparation of 1N and 2N Alcohols with Asymmetric Catalytic Transfer Hydrogenation The 1N ketone prepared in Preparation Example 1 or 2N ketone prepared in Preparation Example 2 (222 mg, 1.0 mmol) was dissolved in a 5:2 formic acid-triethylamine azeotrope (1.4 mL) and subjected to an argon environment. After the solution was cooled to 0° C. in the argon environment, chloro{[(1S,2S)-(+)-amino-1,2-diphenylethyl](4-toluenesulfonyl)amido}(p-cymene)ruthenium(II) (2 mg, 0.003 mmol) of Chemical Formula 7 was added thereto. Stirring at room temperature for 48 h was followed by extraction with ethyl acetate (2 mL) to give the results of Table 8, below.

TABLE 8

| Example No. | Reactant | Product | Conversion Rate [%] | Optical Purity [%] |
|---|---|---|---|---|
| 47 | 1N Ketone | 1N Alcohol | 99.0 | 91.4 |
| 48 | 2N Ketone | 2N Alcohol | 99.0 | 87.8 |

Preparation of Carbamate

Preparation Example 49

Preparation of Carbamic Acid (R)-1-(2-Chlorophenyl)-2-(tetrazol-1-yl)ethyl ester To PBS (1000 mL, pH 7.0) containing 5% (w/v) glycerol were added baker's yeast (50 g) and 1N ketone (10 g, 44.9 mmol) prepared in preparation example 1, together with nicotineamide adenine dinucleotide (NAD, 1 mg). The resulting reaction suspension was stirred at 30° C. for 4 days and mixed with ethyl acetate (500 mL). After being separated, the organic layer thus formed was washed with 10% brine (3×500 mL). To the organic layer was added magnesium sulfate, followed by filtering the resulting suspension. The filtrate was distilled under reduced pressure to afford 8.5 g of a solid residue which was then dissolved at 45° C. in ethyl acetate (10 mL) and cooled to room temperature. Slow addition of heptane (20 mL) led to crystallization. The precipitate thus formed was filtered and washed to give 7.32 g (32.6 mmol) of 1-(2-chlorophenyl)-2-(1,2,3,4-tetrazol-1-yl)ethan-1-ol (optical purity 99.9%). The precipitate was dissolved in dichloromethane (73 mL) to which methanesulfonic acid (5.5 mL, 84.7 mmol) was added at 10° C., followed by the slow addition of sodium cyanate (4.24 g, 65.2 mmol). The reactant mixture was stirred at 10° C. for 12 h and washed with 10% brine (3×100 mL) The organic layer thus formed was concentrated under reduced pressure and the concentrate was dissolved in isopropanol (14 mL). Heating the solution to 45° C. and cooling to room temperature led to the completion of crystallization. The precipitate thus obtained was filtered and washed to afford 7.84 g (29.3 mmol) of carbamic acid (R)-1-(2-chlorophenyl)-2-(tetrazol-1-yl)ethyl ester (purity >99.0%, optical purity >99.0%).

$^1$H-NMR(Acetone-$d_6$) d9.14(s, 1H), d7.31-7.59(m, 4H), ☐6.42(m, 1H), d6.0-6.75(Br, 2H), d4.90(d, 1H), d5.03(m, 2H)

Preparation Example 50

Preparation of Carbamic Acid (R)-1-(2-Chlorophenyl)-2-(tetrazol-2-yl)ethyl ester The 2N ketone (15.5 g, 69.6 mmol), prepared in Preparation Example 2, was dissolved in a 5:2 formic acid-triethylamine azeotrope (60 mL) and subjected to an argon environment. To this solution was added chloro{[(1S,2S)-(+)-amino-1,2-diphenylethyl](4-toluenesulfonyl)amido}(p-cymene) ruthenium(II) of Chemical Formula 7 (140 mg, 0.220 mmol), followed by stirring at room temperature for 48 h. The solution was diluted in ethylacetate (200 mL) and washed with 10% brine (3×100 mL). The organic layer thus formed was dried over magnesium sulfate and filtered and the filtrate was distilled under reduced pressure to give 14.8 g (65.9 mmol) of 1-(2-chlorophenyl)-2-(1,2,3,4-tetrazol-2-yl)ethan-1-ol (optical purity 87.8%) as an oily residue. To this was added tetrahydrofuran (150 mL). After cooling to −15° C., chlorosulfonyl isocyanate (6.9 mL, 79.2 mmol) was slowly added and stirred at −10° C. for 2 h. The slow addition of water (10 mL) induced termination of the reaction. The resulting solution was concentrated under reduced pressure until about 100 mL of the solvent was removed. The concentrate was diluted in ethyl acetate (200 mL) and washed with 10% brine (3×150 mL). The organic layer was concentrated under reduced pressure and the concentrate was dissolved in isopropanol (30 mL) to which heptane (90 mL) was slowly added, leading to the completion of crystallization. The precipitate thus obtained was filtered and washed to afford 15.4 g (57.5 mmol) of carbamic acid (R)-1-(2-chlorophenyl)-2-(tetrazol-2-yl) ethyl ester (purity >99.0%, optical purity>99.0%).

$^1$H-NMR(Acetone-$d_6$) d8.74(s, 1H), d7.38-7.54(m, 4H), d6.59(m, 1H), d6.16(Br, 2H), d4.90(d, 1H), d5.09(m, 2H)

As described hitherto, carbamate compounds with high optical and chemical purity can be produced with an economical benefit in accordance with the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing carbamic acid 1-aryl-2-tetrazolyl ethyl ester, represented by Chemical Formula 1, comprising:

subjecting an arylketone, represented by Chemical Formula 2, to (R)-selective asymmetric reduction to form an alcohol compound of (R)-configuration, represented by Chemical Formula 3; and
carbamating said alcohol:

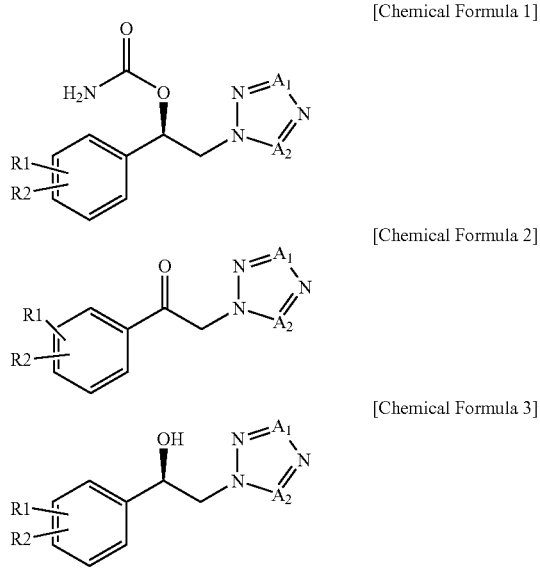

[Chemical Formula 1]

[Chemical Formula 2]

[Chemical Formula 3]

wherein, $R_1$, and $R_2$ are independently selected from a group consisting of hydrogen, halogen, perfluoroalkyl, an alkyl of 1 to 8 carbon atoms, a thioalkoxy of 1 to 8 carbon atoms, and an alkoxy of 1 to 8 carbon atoms;

one of $A_1$ and $A_2$ is CH with the other being N; wherein said (R)-selective asymmetric reduction is achieved by biological asymmetric reduction that is carried out in a buffer containing the arylketone of Chemical Formula 2, a microbial strain producing oxidoreductase that is selected from a group consisting of yeasts of *Candida* genus including *Candida parapsilosis* and *Candida rugosa*; yeasts of *Pichia* genus including *Pichia anomala* and *Pichia jadinii*; yeasts of *Saccharomyces* genus including Baker's yeast, *Saccharomyces cerevisiae* and *Saccharomyces pastorianus*; yeasts including *Rhodotorula mucilaginosa* and *Trigonopsis variabilis*; bacteria including *Klebsiella pneumoniae, Enterobacter cloacae, Erwinia herbicola, Micrococcus luteus, Bacillus stearothermophilus, Rhodococcus erythropolis* and *Rhodococcus rhodochrous*; fungi including *Mucor racemosus* and *Geotrichum candidum*; and a combination thereof, and a cosubstrate; or said (R)-selective asymmetric reduction is achieved by chemical asymmetric reduction with a chiral borane reductant, or by asymmetric catalytic hydrogenation, or by asymmetric catalytic transfer hydrogenation.

2. The method according to claim 1, wherein the chiral borane reductant is (–)-B-chlorodiisopinocampheylborane or (R)-2-methyl-CBS-oxazaborolidine/borane.

3. The method according to claim 1, wherein the asymmetric catalytic hydrogenation is carried out by reacting the arylketone of Chemical Formula 2 with hydrogen gas in the presence of (R)-bisphosphono-ruthenium(II)-(R,R)-chiral diamine complex catalyst.

4. The method according to claim 1, wherein the asymmetric catalytic transfer hydrogenation is carried out by reacting the arylketone of Chemical Formula 2 with formic acid triethylamine or isopropanol-inorganic base in the presence of a [S,S]-monosulfonatediamine-M(II)-arene complex catalyst system, wherein M represents ruthenium or rhodium.

5. The method according to claim 1, wherein the carbamating step is carried out by reacting the alcohol compound of (R)-configuration of Chemical Formula 3 with inorganic cyanate and an organic acid.

6. The method according to claim 1, wherein the carbamating step is carried out by hydrolyzing a product resulting from reaction between the alcohol compound of (R)-configuration of Chemical formula 3 and an isocyanate compound selected from the group consisting of chlorosulfonic isocyanate, trichloroacetyl isocyanate and trimethylsilyl isocyanate.

7. The method according to claim 1, wherein the carbamating step is carried out by introducing ammonia into a product resulting from reaction between the alcohol compound of (R)-configuration of Chemical formula 3 and a carbonyl compound comprising 1,1'-carbonyldiimidazole, carbamoylhalide, N,N'-disuccinimidyl carbonate, phosgene, triphosgene or chloroformate.

8. The method according to claim 1, further comprising a crystallizing step after at least one of the (R)-selective asymmetric reduction step and the carbamating step.

9. The method according to claim 8, wherein the crystallizing step comprises:
adding to a reaction product a solubilizing agent selected from among acetone, acetonitrile, tetrahydrofuran, ethylacetate, dichloromethane, chloroform, 1,4-dioxane, a lower alcohol of 1 to 4 carbon atoms and a mixture thereof; and
adding a precipitating agent thereto selected from the group consisting of water, a lower alcohol of 1 to 4 carbon atoms, diethylether, pentane, hexane, cyclohexane, heptane and a mixture thereof.

10. The method according to claim 1, additionally including the step of preparing the arylketone of Chemical Formula 2 that is prepared by substitution reaction between an arylketone of the following Chemical Formula 4 with a tetrazole of the following Chemical Formula 5:

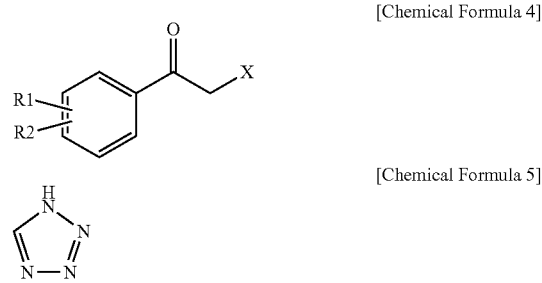

[Chemical Formula 4]

[Chemical Formula 5]

wherein, $R_1$ and $R_2$ are as defined in claim 1; and

X is a leaving group selected from among a halide and a sulfonate.

11. The method according to claim 10, further comprising a crystallizing step comprising:
adding a solubilizing agent selected from among acetone, acetonitrile, tetrahydrofuran, ethylacetate, dichloromethane, chloroform, 1,4-dioxane, a lower alcohol of 1 to 4 carbon atoms and a mixture thereof to a product obtained by the substitution reaction; and adding a precipitating agent selected from water, a lower alcohol of 1 to 4 carbon atoms, diethylether, pentane, hexane, cyclohexane, heptanes and a mixture thereof.

12. A method for preparing an alcohol compound, represented by the following Chemical Formula 3, through (R)-selective asymmetric reduction of an arylketone, represented by the following Chemical Formula 2, wherein the (R)-selective asymmetric reduction is achieved by biological asymmetric reduction or chemical asymmetric reduction:

[Chemical Formula 2]

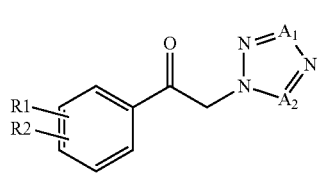

[Chemical Formula 3]

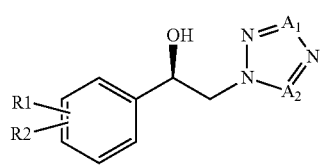

wherein, $R_1$, and $R_2$ are independently selected from a group consisting of hydrogen, halogen, perfluoroalkyl, an alkyl of 1 to 8 carbon atoms, a thioalkoxy of 1 to 8 carbon atoms, and an alkoxy of 1 to 8 carbon atoms; and one of $A_1$, and $A_2$ is CH with the other being N; wherein said (R)-selective asymmetric reduction is achieved by biological asymmetric reduction that is carried out in a buffer containing the arylketone of Chemical Formula 2, a microbial strain producing oxidoreductase that is selected from a group consisting of yeasts of *Candida* genus including *Candida parapsilosis* and *Candida rugosa*; yeasts of *Pichia* genus including *Pichia anomala* and *Pichia jadinii*; yeasts of *Saccharomyces* genus including Baker's yeast, *Saccharomyces cerevisiae* and *Saccharomyces pastorianus*; yeasts including *Rhodotorula mucilaginosa* and *Trigonopsis variabilis*; bacteria including *Klebsiella pneumoniae*, *Enterobacter cloacae*, *Erwinia herbicola*, *Micrococcus luteus*, *Bacillus stearothermophilus*, *Rhodococcus erythropolis* and *Rhodococcus rhodochrous*; fungi including *Mucor racemosus* and *Geotrichum candidum*; and a combination thereof, and a cosubstrate; or said (R)-selective asymmetric reduction is achieved by chemical asymmetric reduction with a chiral borane reductant, or by asymmetric catalytic hydrogenation, or by asymmetric catalytic transfer hydrogenation.

* * * * *